(12) United States Patent
Ein-Gal

(10) Patent No.: US 7,748,902 B1
(45) Date of Patent: Jul. 6, 2010

(54) STATIONARY SOURCE RADIOTHERAPY

(76) Inventor: Moshe Ein-Gal, 30 Azar Street, Ramat Hasharon 47203 (IL)

( * ) Notice: Subject to any disclaimer, the term of this patent is extended or adjusted under 35 U.S.C. 154(b) by 0 days.

(21) Appl. No.: 12/324,867

(22) Filed: Nov. 27, 2008

(51) Int. Cl.
*H05G 1/00* (2006.01)
(52) U.S. Cl. .................................. 378/208; 378/65
(58) Field of Classification Search .............. 378/170, 378/177, 179, 180, 208, 65
See application file for complete search history.

(56) References Cited

U.S. PATENT DOCUMENTS 6,863,440 B2 * 3/2005 Sildve et al. ................ 378/208
2009/0161826 A1 * 6/2009 Gertner et al. ............... 378/65

* cited by examiner

*Primary Examiner*—Hoon Song
(74) *Attorney, Agent, or Firm*—Dekel Patent Ltd.; David Klein

(57) ABSTRACT

A radiotherapy system including a stationary radiation source that emits a radiation beam towards an isocenter located at a target, a skull attachment attachable to a patient's skull, a coupler attached to the stationary radiation source and to the skull attachment, wherein the coupler is operable to translate the skull attachment and to rotate the skull attachment about first and second rotational axes of the coupler.

10 Claims, 2 Drawing Sheets

ACHIEVE TARGET POSITIONING AT THE ISOCENTER BY COUPLING THE SKULL ATTACHMENT TO A ROTATION BEARING BY A PATIENT-SPECIFIC ADAPTER.

↓

DIMENSIONS OF PATIENT-SPECIFIC ADAPTER CAUSE TARGET TO COINCIDE WITH THE ISOCENTER UPON ATTACHING THE SKULL ATTACHMENT TO THE SKULL

FIG. 6

STATIONARY SOURCE RADIOTHERAPY

FIELD OF THE INVENTION

The present invention generally relates to radiotherapy systems, and more particularly to a radiotherapy system and a method wherein a skull attachment is directly coupled to a stationary radiation source housing and a motion system rotates the target located at the isocenter about either of two rotational axes.

BACKGROUND OF THE INVENTION

In stereotactic radiosurgery, a target is localized relative to an external reference frame attached to the head. The target is then irradiated from a wide range of orientations. Localization and irradiation are conventionally applied to a recumbent patient. A radiation source, either for imaging or for treatment, rotates in a vertical plane (i.e., about a horizontal rotation axis) about the patient. The patient's couch may be translated for imaging or rotated about a vertical rotational axis for radiation treatment. There is no relative motion between patient and couch. Repeatable source rotations in conjunction with a series of couch orientations result in irradiation through longitudinal arcs relative to the head (e.g., U.S. Pat. Nos. 5,160,337 and 5,189,687). The method of head immobilization depends on the treatment: frame-attached pins are inserted into the skull for a single-fraction radiosurgery, while detachable immobilizers like a biting block and/or a face mask are used for fractionated radiotherapy. The rotating gantry and the couch are cumbersome, expensive and mechanically imperfect due to difficulties in maintaining intersection of the respective rotational axes with each other and with the beam.

Upright head radiotherapy is taught in U.S. Pat. No. 5,250,019. The patient is rotated about a vertical rotational axis while a radiation beam is incremented through elevation angles that intersect the rotational axis at an isocenter. The beam trajectories form concentric cones having a joint apex at the isocenter where the target is placed. However, intersecting the turntable rotational axis with the isocenter presents a mechanical difficulty.

SUMMARY OF THE INVENTION

The present invention seeks to provide an improved radiotherapy system, as is described more in detail hereinbelow.

In accordance with embodiments of the radiotherapy system, and in contrast with prior art systems, a skull attachment is directly coupled via a coupler to a stationary radiation source housing. The coupler is operable to translate the skull attachment so as to bring the target to the isocenter and to rotate the target located at the isocenter about two rotational axes. The coupler can be used to increment the skull attachment orientation relative to the radiation beam during treatment. Target localization, i.e., obtaining relative target position to the skull-attachment, may utilize markers registered to the skull attachment.

Two-dimensional skull orientations relative to the isocenter-intersecting beam, while maintaining the target at the isocenter, are obtained by rotating the skull about two skull rotational axes. The coupler is operable to translate and rotate the skull attachment relative to the isocenter. The coupler is directly attached to the radiation source housing. One of the skull rotations may be continuous (e.g., about a vertical rotational axis), while the other may assume discrete orientations (e.g., about a horizontal rotational axis). In such a case, a turntable is used for rotating the patient so as to follow the continuous rotation about a vertical rotational axis. A possible misalignment between the skull and the turntable rotational axes is small so as not to cause the patient any harm or inconvenience during rotation.

Using a stationary horizontal beam, a family of radiation arcs relative to the skull may be obtained by continuously rotating the skull about a vertical rotational axis while the skull undergoes a discrete set orientations about a horizontal rotational axis. The orientations of the arcs relative to the skull are selected by the orientation of the horizontal rotational axis, e.g., longitudinal arcs are obtained for the horizontal rotational axis being in the sagittal plane, while transversal arcs relate to the horizontal rotational axis being in the coronal plane.

There is thus provided in accordance with an embodiment of the present invention a radiotherapy system including a stationary radiation source that emits a radiation beam towards an isocenter located at a target, a skull attachment attachable to a patient's skull, a coupler attached to the stationary radiation source and to the skull attachment, wherein the coupler is operative to move the skull attachment in translation and rotation along and about first and second rotational axes of the coupler. Both first and second rotational axes preferably intersect the isocenter. The first rotational axis may be horizontal and the second rotational axis may be vertical. The first rotational axis may be in a sagittal plane, in a coronal plane, or in between.

Fiducial markers and/or sensors may be provided for determining a relative position of the target and the skull attachment.

The skull attachment may be at least one of a bite-block, a face mask and a head frame with skull-penetrating fasteners.

Target positioning at the isocenter may be achieved by coupling the skull attachment to a rotation bearing by a patient-specific adapter. The dimensions of the patient-specific adapter cause the target to coincide with the isocenter upon attaching the skull attachment to the skull.

There is also provided in accordance with an embodiment of the present invention a method for radiotherapy including emitting a radiation beam from a stationary radiation source towards an isocenter located at a target, attaching a skull attachment to a patient's skull, wherein a coupler is attached to the stationary radiation source and to the skull attachment, and moving the skull attachment in translation and rotation along and about first and second rotational axes of the coupler.

BRIEF DESCRIPTION OF THE DRAWINGS

The present invention will be understood and appreciated more fully from the following detailed description, taken in conjunction with the drawings in which:

FIG. 6 is a simplified block diagram of target positioning at the isocenter by coupling the skull attachment to a rotation bearing by a patient-specific adapter, in accordance with an embodiment of the present invention.

DETAILED DESCRIPTION OF EMBODIMENTS

Figure 1:
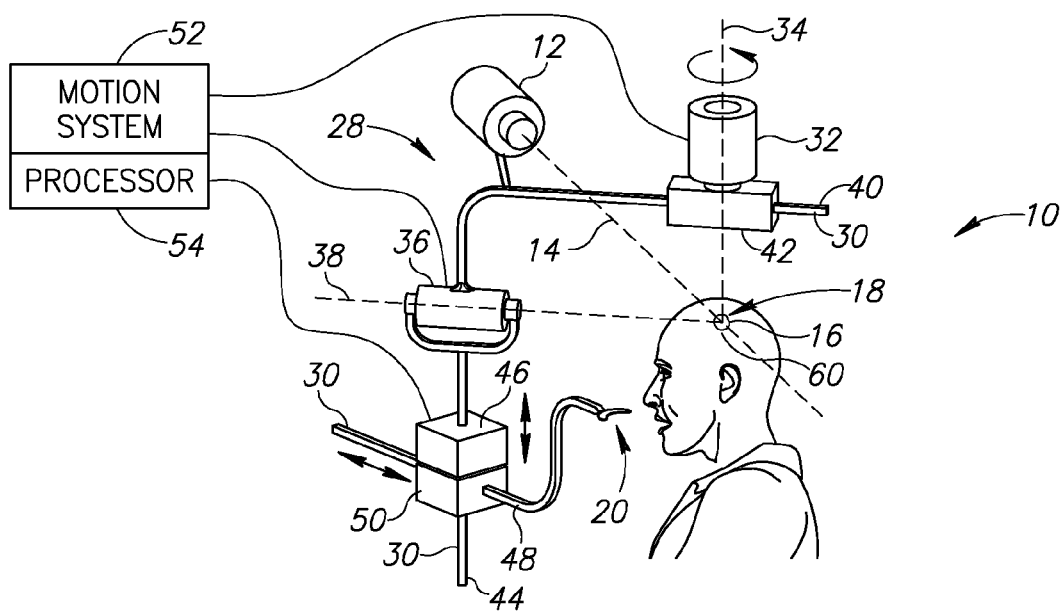
FIG. 1 is a simplified illustration of a radiotherapy system, constructed and operative in accordance with an embodiment of the present invention.

Reference is now made to FIG. 1, which illustrates a radiotherapy system 10, constructed and operative in accordance with a non-limiting embodiment of the present invention.

Radiotherapy system 10 includes a stationary radiation source 12 (any suitable source of radiation, such as but not limited to, x-rays, gamma rays, etc.). Radiation source 12 emits a radiation beam 14 towards an isocenter 16 located at a target 18.

Figure 4:
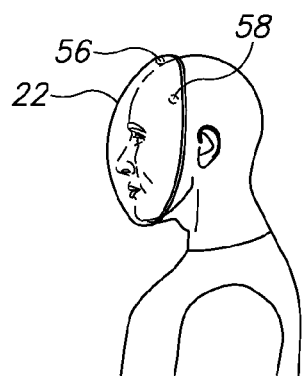
FIGS. 4 and 5 are simplified illustrations of alternate skull attachments, namely, respectively a face mask and a head frame with skull-penetrating pins or screws, in accordance with an embodiment of the present invention.
Figure 5:
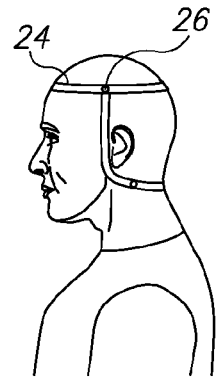

A skull attachment 20 is attached to a patient's skull. In the embodiment illustrated in FIG. 1, skull attachment 20 is a bite block. FIGS. 4 and 5 show alternate skull attachments, namely, respectively a face mask 22 and a head frame 24 with skull-penetrating pins or screws 26. It is noted that the phrase "the skull attachment is attached to the patient's skull" encompasses not just rigid attachment to the skull such as by means of pins or screws, but also any arrangement whereby the skull is at least temporarily immobilized with respect to the attachment, such as in the case of the bite block and face mask. "Biting" the bite-block or pressing the face against the face mask places target 18 at isocenter 16. Subsequently, rotating the bite block or the face mask about the isocenter 16 reorients target 18 relative to radiation beam 14 while keeping target 18 at isocenter 16.

A coupler 28 is attached to stationary radiation source 12 and to skull attachment 20. As will be explained below, coupler 28 translates the skull attachment 20 relative to the isocenter 16, and also rotates skull attachment 20 about two different rotational axes, whereas both rotational axes intersect the isocenter 16.

In the non-limiting illustrated embodiment, coupler 28 includes a frame 30 rigidly attached to stationary radiation source 12. A vertical rotation bearing 32 is provided for rotating skull attachment 20 about a vertical rotational axis 34 (this may be accomplished by turning a turntable upon which the patient sits). Likewise, a horizontal rotation bearing 36 is provided for rotating skull attachment 20 about a horizontal rotational axis 38. Vertical rotation bearing 32 is mounted on a longitudinal arm 40 of frame 30. Arm 40 can slide through a longitudinal block 42 on which vertical rotation bearing 32 is mounted. Horizontal rotation bearing 36 is mounted on a vertical arm 44 of frame 30. Arm 44 can slide through a vertical block 46 on which horizontal rotation bearing 36 is mounted. Bite block 20 is mounted on a lateral arm 48 of frame 30. Arm 48 can slide through a lateral block 50 on which bite block 20 is mounted. Arm 44 can also slide through lateral block 50.

A motion system 52 in communication with a processor 54 is operative to move skull attachment 20 in translation and rotation. That is, motion system 52 can translate skull attachment 20 linearly along any of arms 40, 44 and 48 (which are three mutually orthogonal coordinates) and rotate skull attachment 20 about either of axes 34 and 38. Motion system 52 includes, without limitation, linear motors and encoders, rotary motors and encoders, accelerometers and control and feedback apparatus, for example. Processor 54 synchronizes respective motions of motion system 52 and coupler 28.

Since the relative position of target 18 and skull attachment 20 is fixed, target positioning is implemented by positioning skull attachment 20 with motion system 52. The relative position may be obtained by CT and/or other imaging of target 18 and markers 56 (shown exemplary in FIG. 4) placed on skull attachment 20. Another method for obtaining the relative position is to place sensors 58 (shown exemplary in FIG. 4) on skull attachment 20, where the sensors 58 are operable to sense radiation emitted by emitters 60 implanted in target 18. Accordingly, in order to place target 18 at isocenter 16, the skull attachment 20 may be moved to some position relative to isocenter 16, and skull attachment 20 may be attached to the patient. Rotating skull attachment 20 about isocenter 16, with target 18 placed at the isocenter, reorients target 18 relative to the stationary radiation source 12.

Alternatively, as shown in block diagram form in FIG. 6, target positioning at the isocenter may be achieved by coupling the skull attachment to a rotation bearing by a patient-specific adapter. The dimensions of the patient-specific adapter cause the target to coincide with the isocenter upon attaching the skull attachment to the skull.

For incrementing target orientation, the skull may be detached from skull attachment 20, whereupon the attachment orientation is incremented and the patient is re-attached to skull attachment 20.

Two-dimensional beam orientations relative to the skull are obtained by rotating the skull about two skull rotational axes 34 (azimuth) and 38 (rotation or elevation, depending on the person's point of view) intersecting the isocenter 16, while maintaining the target 18 at the isocenter 16. One of the skull rotations may be continuous (e.g., about vertical rotational axis 34), while the other may include discrete orientations about horizontal rotational axis 38. In such a case, a turntable (part of motion system 52) is used for rotating the patient so as to follow the continuous rotation about vertical rotational axis 34. The discrepancy between the skull and the turntable rotations is small so as not to cause the patient any harm or inconvenience.

Figure 2:
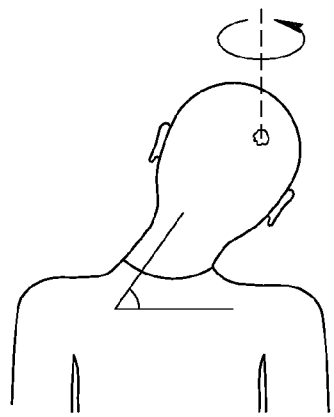
FIGS. 2 and 3 are simplified illustrations of tilting a skull with the system of FIG. 1 about two different rotation axes.
Figure 3:
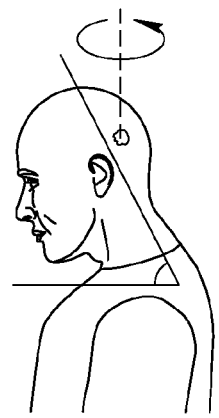

Arc irradiations about vertical rotational axis 34 together with discrete skull orientations about horizontal rotational axis 38 form a family of arcs relative to the skull. The orientations of the arcs relative to the skull depend on the orientation of the horizontal rotational axis 38. For example, longitudinal arcs are obtained when horizontal rotational axis 38 is in the sagittal plane (FIG. 2), while transverse arcs are obtained when horizontal rotational axis 38 is in the coronal plane (FIG. 3).

The scope of the present invention includes both combinations and subcombinations of the features described hereinabove as well as modifications and variations thereof which would occur to a person of skill in the art upon reading the foregoing description and which are not in the prior art.

What is claimed is:

1. A radiotherapy system comprising:
   a stationary radiation source that emits a radiation beam towards an isocenter;
   a skull attachment attachable to a patient's skull; and
   a coupler attached to said stationary radiation source and to said skull attachment, wherein said coupler is operative to translate said skull attachment and to rotate said skull attachment about first and second rotational axes, wherein said coupler comprises:
   a first rotation bearing for rotating said skull attachment about a first rotational axis;
   a second rotation bearing for rotating said skull attachment about a second rotational axis;
   a skull attachment arm attachable to said skull attachment, whereas said skull attachment arm is translatable relative to said first rotation bearing;
   a first arm for mounting said first rotation bearing onto, whereas said first arm is translatable relative to said second rotation bearing; and
   a second arm for mounting said second rotation bearing onto, whereas said second arm is attachable to said stationary radiation source.

2. The radiotherapy system according to claim 1, further comprising a motion system that moves said skull attachment in translation and rotation along and about said first and second rotational axes of said coupler.

3. The radiotherapy system according to claim 1, wherein both first and second rotational axes intersect said isocenter.

4. The radiotherapy system according to claim 1, wherein the first rotational axes is horizontal and the second rotational axis is vertical.

5. The radiotherapy system according to claim 1, wherein the first rotational axis is in a sagittal plane.

6. The radiotherapy system according to claim 1, wherein the first rotational axis is in a coronal plane.

7. The radiotherapy system according to claim 1, further comprising at least one of fiducial markers and sensors for determining a relative position of the target and said skull attachment.

8. The radiotherapy system according to claim 1, wherein said skull attachment comprises at least one of a bite-block, a face mask and a head frame with skull-penetrating fasteners.

9. The radiotherapy system according to claim 1, further comprising a turntable for patient rotation and a processor for synchronizing respective rotations of said coupler and said turntable.

10. The radiotherapy system according to claim 1, wherein said skull attachment is coupled to a rotation bearing by a patient-specific adapter, said patient-specific adapter causing a target in a patient's skull to coincide with the isocenter upon attaching said skull attachment to the patient's skull.

* * * * *